United States Patent [19]
Kung

[11] Patent Number: 5,639,785
[45] Date of Patent: Jun. 17, 1997

[54] METHODS FOR THE TREATMENT OF BALDNESS AND GRAY HAIR USING ISOFLAVONOID DERIVATIVES

[75] Inventor: Patrick C. Kung, Cambridge, Mass.

[73] Assignee: Global Pharma, Ltd., Lexington, Mass.

[21] Appl. No.: 484,097

[22] Filed: Jun. 7, 1995

[51] Int. Cl.$^6$ .................................................. A61K 31/35
[52] U.S. Cl. .......................................................... 514/456
[58] Field of Search ............................................. 514/456

[56] References Cited

FOREIGN PATENT DOCUMENTS

WO93/00896  1/1993  WIPO.
WO95/02566  1/1995  WIPO.

OTHER PUBLICATIONS

Merck Index, 10 ed, 1983, #2794, p. 405.
CA 119:146570, 1993.
CA 100:126730, 1983.
Rui, H., "Recent Progress in the Study of Anticancer Drugs Orginating from Plants and Traditional Medicines in China," Chin. Med. Sci. J., vol. 9, No. 1, pp. 61–69 (1994).
Miksicek, R., "Interaction of Naturally Occurring Nonsteroidal Estrogens with Expressed Recombinant Human Estrogen Receptor," J. Steroid Biochem. Molec. Biol., vol. 49, No 2/3, pp. 153–160 (1994).
Higashi, K., et al., "Daidzein Inhibits Insulin—or Insulin–Like Growth Factor–1–Mediated Signaling in Cell Cycle Progression of Swiss 3T3 Cells", Biochimica et Biophysica Acta 1221 (1994) 29–35.
Jing, Y. et al., "Differentiation of Promyelocytic Leukemia Cells HL–60 Induced by Daidzein in Vitro and In Vivo," Anticancer Research, 13: 1049–1054 (1993).
Keung, W.M. et al., "Daidzin and Daidzein Suppress Free–Choice Ethanol Intake by Syrian Golden Hamsters," Proc. Natl. Sci. USA, vol. 90, pp. 10008–10012 (1993).

Keung, W.M. et al., "Daidzin: A Potent, Selective Inhibitor of Human Mitochondrial Aldehyde Dehydrogenase," Proc. Natl. Acad. Sci. USA, vol. 90, pp. 1247–1251 (1993).
Kueng, W.M., "Biochemical Studies of a New Class of Alcohol Dehydrogenase Inhibitors from Radix *pueraiae*," Alcohol Clin. Exp. Res. vol. 17, No. 6 pp. 1254–1260 (1993).
Aldercreutz H. et al., "Dietary Phytoestrogens and Cancer: In Vitro and In Vivo Studies," J. Steroid Biochem. Molec. Biol., vol. 41, No. 3–8, pp. 331–337 (1992).
Lundh, T.J.O. et al., "Uncoupling and Inhibition of the Respiratory Chain in Rat Liver Mitchondria by Some Naturally Occurring Estrogens and Their Metabolites," J. Agric. Food Chem., 1991, 39, 736–739.
Degen, G.H., "Interaction of Phytoestrogens and Other Environmental Estrogens with Prostaglandin Synthase In Vitro," J. Steroid Biochem., vol. 35, Nos. 3/4, pp. 473–479 (1990).
Farmakalidis, E. et al., "Oestrogenic Response of the CD–1 Mouse to the Soya–Bean Isoflavones Genistein, Genistin and Daidzin," Fd. Chem. Toxic., vol. 22, No. 3, pp. 237–239 (1984).
Bartholomew, R.M. et al., "Lack of Mutagenicity of Some Phytoestrogens in the Salmonella/Mammalian Microsome Assay," Mutation Research, 78 (1980) 317–321.
Iyer, R. N. et al., "Synthetic Experiments in the Chromone Group," Proceed. Ind. Acad. Sci., 33A, pp. 116–126 (1951).

Primary Examiner—Rebecca Cook
Attorney, Agent, or Firm—Pennie & Edmonds

[57] ABSTRACT

The present invention relates to novel pharmaceutical compositions of isoflavanoid derivatives useful for the treatment of male pattern baldness and alopecia areata, and their use in promoting the conversion of gray hair to the original pigment in hair follicles. Also described herein are methods for the synthesis of isoflavanoid derivatives.

5 Claims, No Drawings

METHODS FOR THE TREATMENT OF BALDNESS AND GRAY HAIR USING ISOFLAVONOID DERIVATIVES

FIELD OF THE INVENTION

The present invention relates to the use of isoflavonoid derivatives for the treatment of male pattern baldness and alopecia areata, and to promote the conversion of gray hair to the original pigment in hair follicles. Also described herein are methods for their synthesis. More particularly, this invention relates to the methods of making and using substituted benzopyranyl-4-ones.

BACKGROUND OF THE INVENTION

The management of hair loss has been addressed using topical antihypertensive agents such as minoxidil. V. H. Price, J. Amer. Acad. Dermatology, 16, 749–750 (1987). Minoxidil enlarges vellus hair follicles and seems to maintain terminal follicles in the scalps of mammals. After four months of treatment, approximately 25% of patients achieve minimal regrowth of hair. Rogaine®, the only compound approved to date to treat baldness, was developed because the oral administration of the drug stimulated hair growth. (Upjohn Co. Physicians Desk Ref., pp. 2578, 49th Ed (1995). Minoxidil is a substituted pyrimidine. The present invention relates to the use of daidzein, known as 7-hydroxy-3-(4-hydroxyphenyl)-4-H-1-benzopyranyl-4-one. Daidzein is an isoflavone with a variety of pharmacological effects.

Along with isoflavone glycosides, such as daidzin (7-glycoside daidzein), isoflavones are found mostly in leguminous plants. (J. L. Ingham, Naturally Occurring Isoflavonoids, Vol. 43, pp. 1–226, Progress in the chemistry of organic natural products, Ed, W. Herz, H. Grisebach & G. W. Kirby, Springer-Verlag, Wien, New York, 1983). The synthesis of daidzein & its derivatives was reviewed & reported by G. Shao et al (Yao Hsueh Hsueh Pao 15(9), 538, 1980; Q. E. Ji and Y. L. Wei, Yao Hsueh Hsueh Pao 24(12), 906, 1989). They demonstrated that some of these isoflavones protected mice from hypoxia and increased their coronary blood flow. Some of the isoflavones including daidzein tested negative in mutagenicity using the Salmonella and mammalian microsomal assay (R. M. Bartholomew, D. S. Ryan, Mutat. Res. 78(4), 317, 1980).

Synthetically made daidzein was approved as a pharmaceutical agent in China in 1986 (Health Bureau of Liao Ning Province Approved Drug number; (86)772-2-2). The main indication is hypertension.

Daidzein and its derivatives were also shown to have estrogenic effects (E. Farmakalidis, Food Chem, Toxicol 22,237, 1984). In a recent study, daidzein, equol and lignan were found to compete with estradiol for binding to the rat uterine type II estrogen binding site (H. Aldercreutz et al, J. Steroid Biochem. Mol. Biol. 41(3–8): 331, 1992) and to human recombinant estrogen receptor (ibid 49(2–3): 153, 1994). The estrogenic effects are very mild and become significant only with high doses or prolonged treatment. G. H. Degan (J. Steroid Biochem 35(3–4): 473, 1990) reported that daidzein and three other isoflavones stimulated microsomal prostaglandin synthetase.

Y. Jing et al (Anti-cancer Research 13(4): 1049, 1993) reported that greater than 10 µg/ml of daidzein inhibited the growth of HL60 human leukemia cells. The potent differentiation inducing activity of daidzein was also recently reviewed by R. Han (Chinese Medical Sciences. J.9(1): 61, 1994). Isoflavones, genistein, biochanin A, but not daidzein, inhibited both serum and epidermal growth factor-stimulated growth of LNCaP and Du-145 human prostate cancer cell lines.

Daidzein was also shown to inhibit insulin or insulin growth factor-1 (IGF-1)-mediated signaling in cell cycle progression of Swiss 3T3 cells. It was suggested that the blocking of the G1 phase cell cycle was attributed to the inhibition of casein kinase II enzyme activity by daidzein. The enzyme is required for the commitment of mitogenic signal by insulin or IGF-1 in G1 phase. (K. Higashi and H. Ogawara, Biochim et Biophysica Acta 1221(1): 29, 1994).

Isoflavones have been claimed to exhibit antifibrile, antispasmodic, antihypertensive, and anti-dysrhythmic activities. Until recently, an effect of isoflavones on ethanol drinking behavior had never been demonstrated. In 1993, W-M Keung and B. L. Vallee published a series of studies on the implication of isoflavones, especially daidzin and daidzein, in the treatment of alcohol abuse. They found that daidzin and daidzein suppressed free choice ethanol intake, and did not significantly affect the body weight, water or food intake of Syrian Golden hamsters tested (W-M Keung and B. L. Vallee, PCT Patent Publication No. W093/00896; Proc. Natl. Acad. Sci. USA 90:10008, 1993). This work was based on the use of folklore herbal medicine, Radix puerariae (RP) prepared from the root of leguminosae Pueraria lobota (commonly known as kudzu), for anti-drunkenness effect. RP is a rich source of isoflavones. Daidzein and genistein, isolated from RP, are reversible inhibitors of alcohol dehydrogenase (ADH) class I isozymes. The Ki of daidzein for $r_1r_1$ and $r_2r_2$ ADH isozymes is about 1 µM. The inhibition is competitive with respect to ethanol, but uncompetitive with respect to NAD (W-M Keung and B. L. Vallee, Alcohol Clin. Exp. Res. 17(6) 1254, 1993; i.b.d. Prod. Natl. Acad. Sci USA 90, 1247, 1993). They reported that daidzin did not inhibit ADH; it was, however, a potent inhibitor of aldehyde dehydrogenase (ALDH) II and II of human mitochondria. They further suggested that the isoflavones could stimulate ethanol oxidation by increasing $NAD^+$ regeneration via accelerated respiration because daidzein and several other isoflavones exerted significant uncoupling effect of oxidative phosphorylation in vitro with resting state mitochondria. (J. J. O. Lundh and B. O. Lundgren, J. Agricult, Food Chem. 39: 736, 1991).

SUMMARY OF THE INVENTION

The substituted isoflavonoids of this invention are useful in the treatment of hair loss and in the conversion of hair color to its original pigment, and are represented by the formula (I)

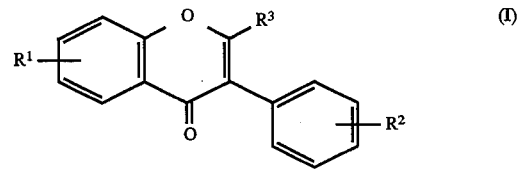

wherein $R^1$ represents hydrogen, hydroxy, alkoxy of 1–6 carbon atoms, alkyl of 1–6 carbon atoms, OCOR where R is alkyl of 1–6 carbon atoms or phenyl; $R^2$ is hydrogen, hydroxy, alkoxy of 1–6 carbon atoms, alkyl of 1–6 carbon atoms, OCOR where R is alkyl of 1–6 carbon atoms or phenyl; $R^3$ is hydrogen; and pharmaceutically acceptable salts thereof.

DETAILED DESCRIPTION OF THE INVENTION

Compounds of the formula (I) where $R^1$ and $R^2$ are hydroxy and $R^3$ is hydrogen may be prepared generally by the modification of procedures published by Iyer (R. N. Iyer, Proceed. Ind. Acad. Sci. 33A, 116, 1951) and Farkas (L. Farkas, et al., Berichte Dtsch Chem., Gcs 92, 819–821) and are hereby incorporated by reference.

As shown in Scheme I below, p-hydroxy phenylacetic acid (2) is reduced with resorcinol (1) in the presence of anhydrous zinc chloride to produce the ketone (3). Other suitable catalysts include, but are not limited to, aluminum chloride, boron trifluoride etherate, boron trifluoride, antimony chloride and ferric chloride. The ketone (3) is treated with N,N-dimethylformamide dimethyl acetal in dimethylformamide to afford daidzein (4). The cyclization of the ketone (3) to daidzein (4) can also be effected with N,N-dimethylformamide di-tert-butyl acetal, N,N-dimethylformamide di-cyclohexyl acetal, N,N-dimethylformamide di-ethyl acetal, N,N-dimethylformamide diisopropyl acetal, and N,N-dimethylformamide di-neopentyl acetal.

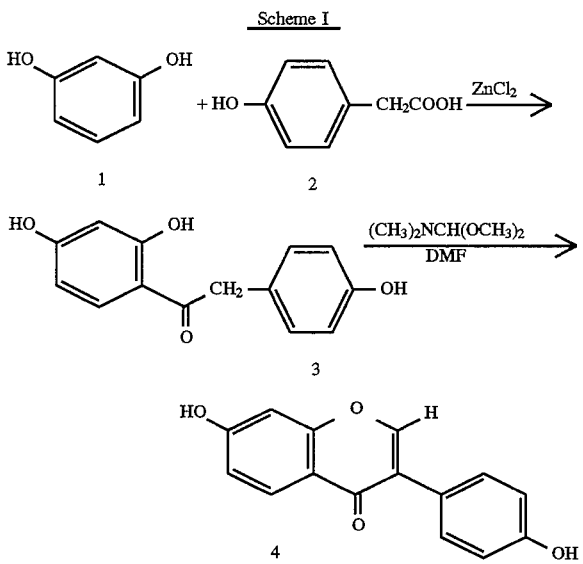

Other isoflavonoid derivatives of the type of formula (I) exhibiting the hair growth promoting activity of daidzein may be prepared by the approach of a multiple component combinatorial array synthesis by adding side chains to the daidzein core structure (R. W. Armstrong, PCT Patent Publication No. WO95/02566, published Jan. 26, 1995), and are hereby incorporated by reference.

The present invention includes pharmaceutically acceptable salts of the compounds of formula (I). Non-toxic salts of the compounds of the above-identified formulas formed with organic or inorganic bases are also included within the scope of this invention and they include, for example, those of alkali metals, such as sodium, potassium and lithium. The salts are prepared by conventional means as, for example, by treating a compound of formula (I) with an appropriate base. Illustrative examples of compounds of this invention are shown in Table I. In addition, an extract of *Pueraria lobata* containing a sufficient concentration of daidzein, may also be used for the practice of the present invention.

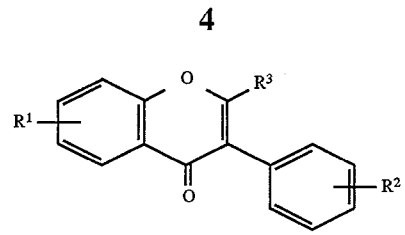

TABLE I

| Example | $R^1$ | $R^2$ | $R^3$ | M.P. (°C.) |
|---|---|---|---|---|
| 1 | 7-OH | 4-OH | H | 315–323 |
| 2 | 6-OH | 4-OH | H | — |
| 3 | 5-OH | 4-OH | H | — |
| 4 | 7-OCOCH$_3$ | 4-OH | H | — |
| 5 | 7-OCH$_3$ | 4-OH | H | — |
| 6 | 7-OPh | 4-OH | H | — |
| 7 | 7-OCOPh | 4-OH | H | — |
| 8 | 6-OCOCH$_3$ | 4-OH | H | — |
| 9 | 5-OCOCH$_3$ | 4-OH | H | — |
| 10 | 7-OH | 3-OH | H | — |
| 11 | 7-OH | 2-OH | H | — |
| 12 | 7-OCOCH$_3$ | 3-OH | H | — |
| 13 | 6-OCOCH$_3$ | 3-OH | H | — |
| 14 | 7-OCH$_3$ | 3-OH | H | — |
| 15 | 7-OPh | 3-OH | H | — |
| 16 | 7-OCOPh | 3-OH | H | — |
| 17 | 7-OH | 3-OCH$_3$ | H | — |
| 18 | 7-OH | 4-OCH$_3$ | H | — |
| 19 | 7-OH | 4-OCOCH$_3$ | H | — |
| 20 | 7-OH | 4-OCOPh | H | — |

The compounds of this invention are useful as agents to treat male pattern baldness and to promote the conversion of gray hair to the original pigment in hair follicles. They may be administered with suitable pharmaceutical carriers and can be in solid or liquid dosage form such as tablets, capsules, powders, soft gels, solutions, suspensions, emulsions, creams or ointments. A further object of this invention is to supply the compounds of this invention in a controlled-release formulation.

The compounds of this invention can be administered orally, parenterally, for example, subcutaneously, intravenously, intramuscularly, intraperitoneally, by intranasal instillation or by application to mucous membranes via an aerosol spray or by application to the scalp or skin by ointment or a cream.

The quantity of compound administered will vary depending on the patient and the mode of administration and can be any effective amount. The quantity of compound administered may vary over a wide range to provide in a unit dosage an effective amount from about 0.001 to 20 mg/kg of body weight of the patient per day to achieve the desired effect. For example, the desired affect can be obtained by consumption of a unit dosage form such as a tablet containing 1–200 mg of a compound of this invention taken 1–3 times daily.

A further object of this invention relates to a method of producing tablets of 7-hydroxy-3-(4-hydroxy-phenyl)-4-H-1-benzopyranyl-4-one.

Tablets of 7-hydroxy-3-(4-hydroxy-phenyl)-4-H-1-benzopyranyl-4-one have various clinical applications in treating central nervous system and hypertension diseases such as faintness, dizziness, stress, hand and leg numbness. They can also reduce whole blood viscosity, and reduce resistance in peripheral blood vessels. They also increases blood transport capacity and improve blood supply to certain organs. The active ingredient, 7-hydroxy-3-(4-hydroxy-phenyl)-4-H-1-benzopyranyl-4-one is non-toxic.

However, the bioavailability of tablets of 7-hydroxy-3-(4-hydroxy-phenyl)-4-H-1-benzopyranyl-4-one produced in the past was not optimal due to their slow dissolution rate and the large size of the crystal of 7-hydroxy-3-(4-hydroxy-phenyl)-4-H-1-benzopyranyl-4-one produced by recrystallization in ethanol (L. J. Tang, P. X. Qiao, L. Y. Zhang, Yao Hsueh Hsueh Pao 24(10): 778, 1989; Table II). The tablets taken by subjects in Examples 3, 4 and 5 were made of 100 mg of nonpulverized daidzein crystals, starch (main excipient), dextrin and magnesium stearate.

An object of the present invention is to provide a method of producing tablets of 7-hydroxy-3-(4-hydroxy-phenyl)-4-H-1-benzopyranyl-4-one. The tablets made by the method of the present invention may manifest improved bioavailability and demonstrate a significant clinical effect.

A method of the present invention comprises pulverizing the raw material of the active ingredient, such as a powder of 7-hydroxy-3-(4-hydroxy-phenyl)-4-H-1-benzopyranyl-4-one produced by the synthetic process described herein, to a microcrystalline product with a particle size not greater than 4 microns (Table II), mixing with an appropriate amount of carrier such as lactose, vitamins, starch, microcrystalline cellulose, inorganic salts and a surfactant (e.q. Tween 80), agglomerating and drying the mixture, adding magnesium stearate (lubricant), and forming tablets as described in Modern Pharmaceutics, G. S. Barber and C. T. Rhodes (1979) (Marcel Dekker, Inc. New York, N.Y.). The pulverized raw materials along with the appropriately chosen excipients should increase the bioavailability of the formulated tablets significantly.

TABLE II

| Down-Sizing Daidzein Crystals with Airjet Pulverizer* | |
| --- | --- |
| Before Processing | 40.8 um+ |
| After Processing | 3.81 um |

* The Airjet Pulverizer (Model QS 50: 0.85/10) used to downsize the daidzein crystals was purchased from the No.3 Chemical Engineering Mechanical Instrument Factory, Shanghai, China.
+ The Average size of the crystals examined under the microscope. um: micrometer.

EXAMPLE 1

A: Preparation of Dimethylamino-methoxy-sulfuric Acid Methyl Ester 10 ml of dimethylformamide is added to 12 ml methyl sulfate. The resulting solution is allowed to react at 65° to 70° C. for 2 hours.

B: Preparation of 7-hydroxy-3-(4-hydroxy-phenyl)-4-H-1-benzopyranyl-4-one

Sodium methoxide (35%) 6.48 g is added into 50 ml dimethylformamide. The mixture is distilled to eliminate methyl alcohol. The resulting product is cooled to less than 20° C. Dimethylamino-methoxy-sulfuric acid methyl ester is added dropwise to the cooled product. The mixture is allowed to react for 5 hours. Under reduced pressure, the reaction mixture is subjected to distillation to remove the dimethylformamide from the mixture. Water is then added to the reaction mixture which yields 7-hydroxy-3-(4-hydroxy-phenyl)-4-H-1-benzopyranyl-4-one as a crude product. The crude product is recrystallized from ethanol. 7.62 g of 7-hydroxy-3-(4-hydroxy-phenyl)-4-H-1-benzopyranyl-4-one is obtained.

Yield: 60%; mp: 315°–323° C.

EXAMPLE 2

| | |
| --- | --- |
| Active ingredient (particle size: 4 microns or less) | 100 mg |
| Lactose | 50 mg |
| Starch | 23 mg |
| Microcrystalline cellulose | 2 mg |
| Dicalcium phosphate | 30 mg |
| Surfactant | trace |
| Magnesium stearate | trace |

Pulverizing the raw material of 7-hydroxy-3-(4-hydroxy-phenyl)-4-H-1-benzopyranyl-4-one produces a microcrystal with a particle size of no more than 4 microns. The tablets are formed by adding the appropriate amount of fillers, disintegrating agents or binding agents, such as, lactose, vitamins, starch, inorganic salts, microcrystalline cellulose and a trace of surfactant to make a soft product, agglomerating the soft product, drying the agglomerated product at 80° to 90° C., adding magnesium stearate (lubricant) to the dried product which results in the formation of tablets.

EXAMPLE 3

A hypertensive male Chinese patient (age 72) complained of dizziness and heavy headiness before taking the daidzein tablets. After taking the medicine (oral dosage: 2×100 mg per dose, 3 doses per day) for four months, it was observed that he experienced a significant improvement of his symptoms, and became more mentally alert. In addition, it was discovered that a significant portion of his gray hairs had gradually turned into the original pigment or dark brown color.

EXAMPLE 4

A healthy Chinese male subject (age 61) with normal blood pressure volunteered to take the medicine for observation on hair growth promoting activity at the same dose reported in Example 3. Before taking the medicine he had few hairs left in the frontoparietal area of the head. Three months after taking the medicine, he began to note an increase of hair density in the affected area. During the three to six months of the testing period, he further noted that he had to increase the hair cut frequency to once a month from once every two months. The newly grown hairs in the affected area are mostly dark brown. The response to the medicine is more sensitive in areas with most recent hair loss. The overall increase of the hair density in the affected area is very significant. The observation was terminated at the end of six months. During the observation period, the subject did not experience any untoward effects.

EXAMPLE 5

A healthy Chinese male (age 47) with normal blood pressure volunteered to take the medicine for the same observation as in Example 4 at the dose described above. His hair condition is normal with no baldness. During the six month testing period, he collected in intervals the hair samples from regular daily combing. Before the testing and during the first month of testing, the hair samples collected had two types, namely completely dark brown or completely gray. At around 50 days into the testing period, a new type of hair, partly dark brown and partly gray, began to appear in the hair samples; they represented about 3% of the gray hairs. In this subject, the gray hairs represented about 25% of his total hairs in the samples collected. It is noted that the dark brown part of the new type of hair is always associated with the lower part of the hair shaft. This is easily identifiable because the hair follicles are distinguishable at one end of hair shafts. The quality and thickness of the new type of hair is very similar to the other types of hairs of this subject. The ratio of length of the dark brown part to that of the gray part of the new type of hair varies from 1:5 to 4:1 in the samples collected during the five-month period. This varying ratio may reflect the stages of the growth cycle of each hair follicle examined. The observation was discontinued at the end of five months. No untoward effects were reported.

The present invention is not to be limited in scope by the exemplified embodiments, which are intended as illustrations of individual aspects of the invention. Indeed, various modifications for the invention in addition to those shown and described herein will be come apparent to those skilled in the art from the foregoing description. Such modifications are intended to fall within the scope of the appended claims.

All publications cited herein are incorporated by reference in their entirety.

I claim:

1. A method of converting gray hair to the original pigment in hair follicles of a patient in need thereof which comprises administering to said patient a pharmaceutical composition comprising an effective amount of a compound of formula (I) and a pharmaceutical carrier:

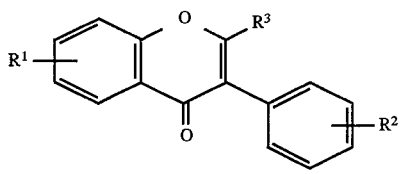

wherein $R^1$ is hydrogen, hydroxy, alkoxy of 1–6 carbon atoms, alkyl of 1–6 carbon atoms, OCOR where R is alkyl of 1–6 carbon atoms or phenyl; $R^2$ is hydrogen, hydroxy, alkoxy of 1–6 carbon atoms, alkyl of 1–6 carbon atoms, OCOR where R is alkyl of 1–6 carbon atoms or phenyl; $R^3$ is hydrogen; or a pharmaceutically acceptable salt thereof.

2. A method of converting gray hair to the original pigment in hair follicles of a patient in need thereof which comprises administering to said patient a pharmaceutical composition comprising an effective amount of a compound of formula (I) and a pharmaceutical carrier:

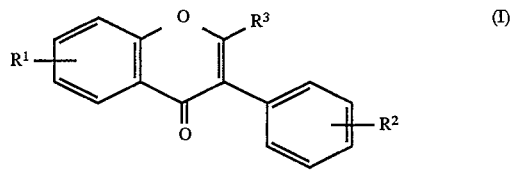

wherein $R^1$ is hydrogen or alkoxy of 1–6 carbon atoms, $R^2$ is hydroxy or alkoxy of 1–6 carbon atoms and $R^3$ is hydrogen.

3. A method of converting gray hair to the original pigment in hair follicles of a patient in need thereof which comprises administering to said patient a pharmaceutical composition comprising an effective amount of a compound of formula (I) and a pharmaceutical carrier:

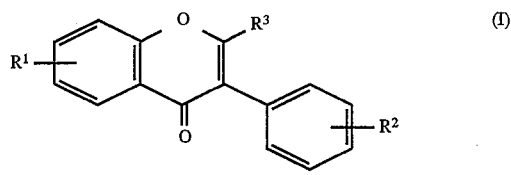

wherein $R^1$ is 7-hydroxy, $R^2$ is 4-hydroxy and $R^3$ is hydrogen.

4. The method of claim 3 wherein the carrier is an ointment.

5. The method of claim 3 wherein the carrier is a cream.

* * * * *